Nov. 29, 1932. E. J. LE DUC Plant Pat. 45
VARIETY OF ROSE
Filed Sept. 29, 1931
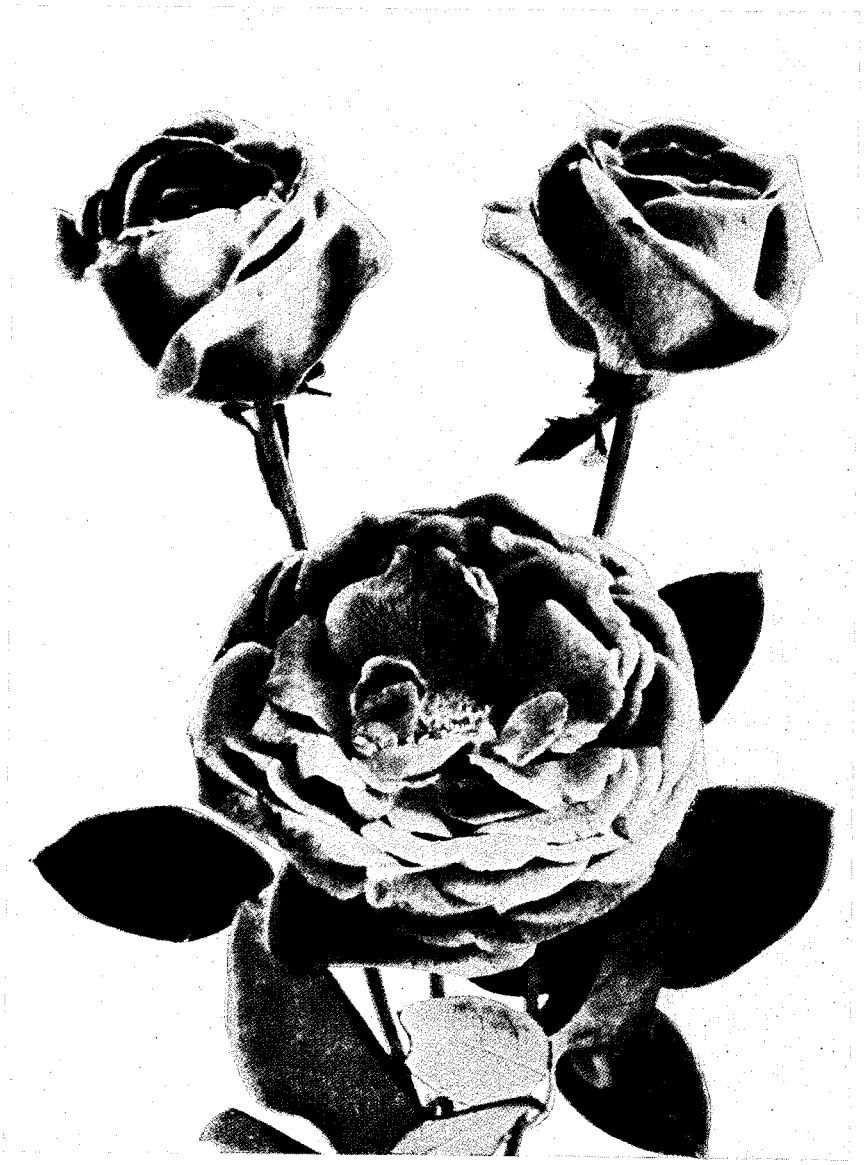
Inventor
Emile J. Le Duc
By Robert Robb
Attorney Patented Nov. 29, 1932

Plant Pat. 45

UNITED STATES PATENT OFFICE

EMILE J. LE DUC, OF DANVILLE, PENNSYLVANIA

VARIETY OF ROSE

Application filed September 29, 1931. Serial No. 566,843.

The present invention relates to a new variety of rose, the novel characteristics of which resides, in the greatest measure, in the strength of growth and in the productivity of the plant.

From the standpoint of the trade, particularly the cut flower trade, it is well known that the majority of roses are not good producers,—that is to say, the number of buds or blossoms produced per annum or other definite period, is relatively small and naturally the return for the care and space required for commercialization is correspondingly restricted. To make up for this lack of productivity in otherwise good plants, a much greater number must be propagated, and, of course, this leads to undue or unprofitable use of time and space.

The present rose, I have found by propagation, possesses the quality of productivity in an unusual or extraordinary degree and hence gives rise to a distinct variety, comparing this characteristic with that of the nearest known variety of which mention is made hereinafter.

Speaking now of the other characteristic referred to above, namely, its strength of growth, it may be stated that this is a desideratum of considerable importance to the florist, for this means ease of handling, so far as the florist is concerned, and greater lasting qualities,—valuable to the purchaser as well as to the florist.

The present rose originated as a "sport" from Scott's Columbia, a well known and extensively grown variety, from which it differs in many important respects, giving rise to a marked improvement or superiority thereover, as well as with reference to the parent of the known variety. In other words, the present rose is shown to grow much larger and stronger, enabling the cutting with longer stems,—an item of considerable value in the market, and among other distinguishing characteristics may be mentioned the fact that this rose is almost thornless,—also making for greater ease in handling.

Another advantageous feature is found in the fact that the foliage is darker than that of the parent and while the flower of the parent variety of this invention is a clear, bright pink, the color in the present instance is a brilliant crimson as it opens, changing to a very dark crimson with scarlet shading, sometimes tending toward royal purple. This color, coupled with the remarkable enduring characteristic of the flower and those characteristics hereinbefore recited in relation to the parent, combine to provide a very desirable and distinctly new commercial product in the rose field. A summary of the descriptive characteristics of this rose is as follows:—

*Bud:*—Large, long-pointed, deep scarlet-crimson with royal purple shadows.

*Flower:*—Extra large, full, double (65 petals), very lasting; quite fragrant, and persisting in its deep scarlet-crimson color as it opens to a remarkably large and full flower of great richness; borne singly on long, strong stems.

*Foliage:*—Medium size, dark green and disease-resistant.

It is to be understood that the foregoing characteristics are typical but subject perhaps to slight variation which may arise by reason of change of environment.

What I claim as new is:

The rose herein shown and described characterized particularly by its large, strong, almost thornless stems, the very dark crimson scarlet shading of its flower and the maintenance of the persistency of these characteristics.

In testimony whereof I affix my signature.

EMILE J. LE DUC.